United States Patent
Reinhardt et al.

(10) Patent No.: US 10,094,803 B2
(45) Date of Patent: Oct. 9, 2018

(54) METHOD AND DEVICE FOR DIAGNOSING THE MEASURING ABILITY OF AN EXHAUST GAS SENSOR

(71) Applicant: Robert Bosch GmbH, Stuttgart (DE)

(72) Inventors: Goetz Reinhardt, Boeblingen (DE); Martin Buchholz, Bietigheim-Bissingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 90 days.

(21) Appl. No.: 15/107,235

(22) PCT Filed: Dec. 3, 2014

(86) PCT No.: PCT/EP2014/076359
§ 371 (c)(1),
(2) Date: Jun. 22, 2016

(87) PCT Pub. No.: WO2015/104101
PCT Pub. Date: Jul. 16, 2015

(65) Prior Publication Data
US 2017/0003249 A1      Jan. 5, 2017

(30) Foreign Application Priority Data
Jan. 7, 2014    (DE) .................. 10 2014 200 068

(51) Int. Cl.
*G01N 27/416*      (2006.01)
*G01N 27/406*      (2006.01)
*G01N 27/407*      (2006.01)

(52) U.S. Cl.
CPC ..... *G01N 27/4163* (2013.01); *G01N 27/4065* (2013.01); *G01N 27/4073* (2013.01)

(58) Field of Classification Search
CPC .......... G01N 27/4163; G01N 27/4073; G01N 27/4065; G01N 27/406–27/41
See application file for complete search history.

(56) References Cited

U.S. PATENT DOCUMENTS 6,767,442 B1 * 7/2004 Scheer ................ G01N 27/419
204/425

FOREIGN PATENT DOCUMENTS

| CN | 101341397 A | 1/2009 |
|---|---|---|
| CN | 101573613 A | 11/2009 |

(Continued)

OTHER PUBLICATIONS

International Search Report dated Feb. 26, 2015 in International Application PCT/EP2014/076359, filed Dec. 3, 2014.

*Primary Examiner* — J. Christopher Ball
(74) *Attorney, Agent, or Firm* — Norton Rose Fulbright US LLP; Gerard Messina

(57) ABSTRACT

A method and device for diagnosing a measuring ability of an exhaust gas sensor in an exhaust gas channel of an internal combustion engine. A sensor design including a storage volume in a reference gas channel, at least one first electrode facing an electrode cavity connected to the exhaust gas channel, and a second electrode facing the reference gas channel is used as the exhaust gas sensor. Such a high voltage is applied between the first electrode and the second electrode during a first phase that the reference gas channel is filled with additional oxygen as a result of decomposition of water and/or carbon dioxide, and a pump current from the first electrode to the second electrode is used to evaluate the measuring ability during a second phase.

6 Claims, 1 Drawing Sheet

(56) References Cited

FOREIGN PATENT DOCUMENTS

| | | |
|---|---|---|
| CN | 102033090 A | 4/2011 |
| DE | 102006062055 | 7/2008 |
| DE | 102006062055 A1 * | 7/2008 |
| DE | 102007057707 | 6/2009 |
| DE | 102008043124 A1 * | 4/2010 ........... G01N 27/419 |
| DE | 102010000663 | 7/2011 |
| DE | 102010000663 A1 * | 7/2011 |
| DE | 102010039188 | 2/2012 |
| DE | 102010039392 | 2/2012 |
| DE | 102011005490 | 9/2012 |

* cited by examiner

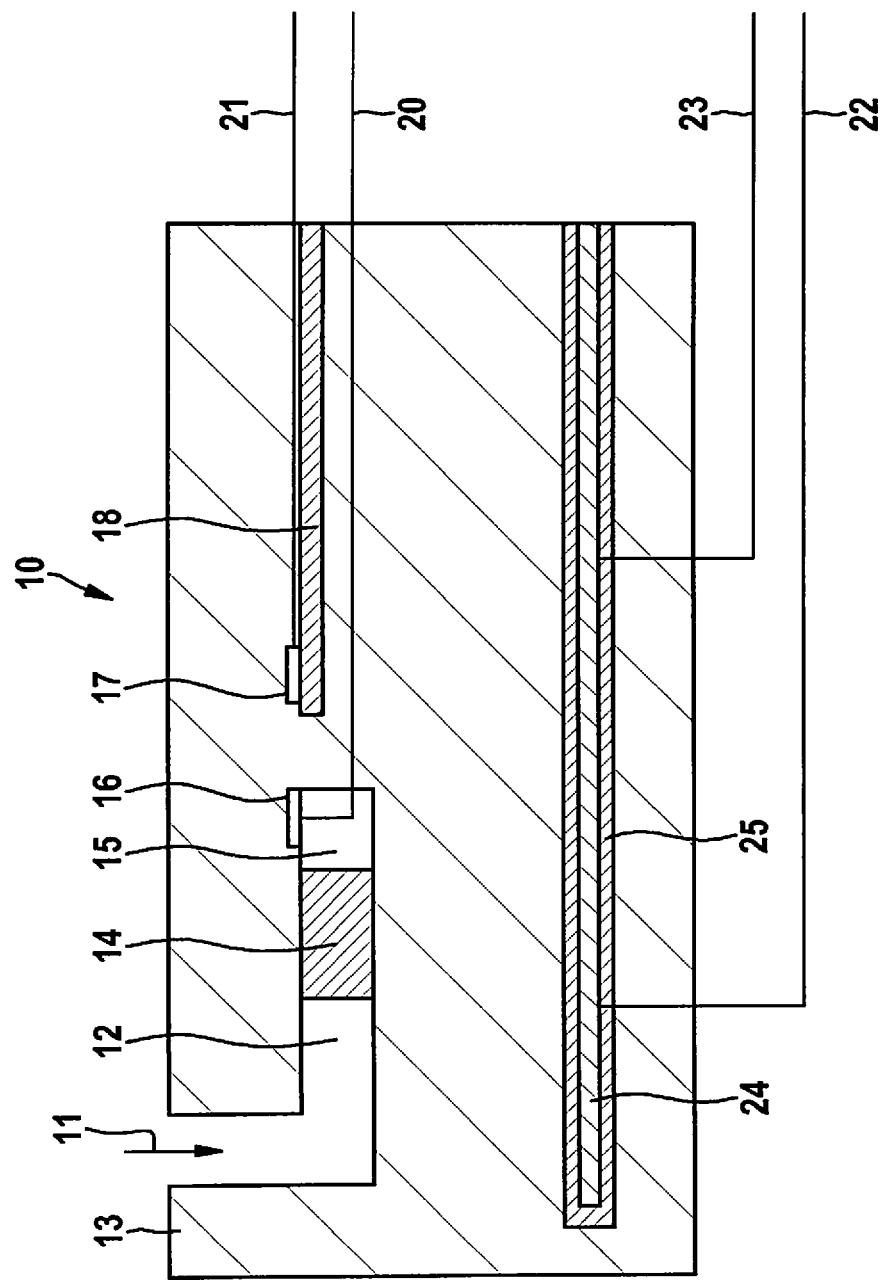

METHOD AND DEVICE FOR DIAGNOSING THE MEASURING ABILITY OF AN EXHAUST GAS SENSOR

FIELD

The present invention relates to a method for diagnosing a measuring ability of an exhaust gas sensor in an exhaust gas channel of an internal combustion engine, a sensor design including a storage volume in a reference gas channel, at least one first electrode facing an electrode cavity connected to the exhaust gas channel and a second electrode facing the reference gas channel being used as the exhaust gas sensor.

The present invention also relates to a device for diagnosing a measuring ability of an exhaust gas sensor in an exhaust gas channel of an internal combustion engine, the exhaust gas sensor including a reference gas channel having a storage volume and at least one first electrode facing an electrode cavity connected to the exhaust gas channel and a second electrode facing the reference gas channel, and a control for acting upon the exhaust gas sensor with voltage signals and current signals and for analysis of voltage signals and current signals being assigned to the exhaust gas sensor.

BACKGROUND INFORMATION

Exhaust gas sensors in the form of lambda sensors are used in the exhaust gas channel of an internal combustion engine to determine the composition of an air-fuel mixture supplied to the internal combustion engine. According to statutory regulations, exhaust gas sensors must be tested for proper functioning during operation, i.e., for a so-called "measuring ability." For this purpose, a gas mixture of a known composition may be supplied to the exhaust gas sensor, and the output signal of the exhaust gas sensor may be evaluated. During testing of a lambda sensor for proper function in the case of a "rich" air-fuel ratio having a lambda value of less than 1, and during testing of the so-called "rich measuring ability," such a mixture would thus have to be supplied to the lambda sensor. In particular in the case of diesel engines, which are operated in the range of a leaner exhaust gas during normal operation, rich operation for a diagnosis results in increased emissions and additional fuel consumption and is therefore preferably avoided. Other possibilities for supplying a rich gas composition to the lambda sensor without intervening in engine operation have not been implementable for a variety of reasons.

However, a reliable diagnosis by another method is also subject to disadvantages. The pump current of the lambda sensor is used to determine the lambda value. The pump current is positive in the case of a lean exhaust gas and is negative in the case of a rich exhaust gas. The transport processes within the lambda sensor with lean exhaust gas and rich exhaust gas differ greatly with regard to the direction of the current, the electrode reaction and gases on the electrodes. For a realistic diagnosis, these conditions must therefore be provided inasmuch as is necessary for the diagnosis.

Exhaust gas sensors may be designed as broadband lambda sensors, lambda step change sensors, dual-cell broadband lambda sensors or single-cell limiting current sensors. Single-cell limiting current sensors may have the particular feature of containing a large reference gas channel for oxygen storage.

German Patent Application No. DE 102011005490 A1 describes a method for operating a sensor element for detecting at least one property of a gas in a measuring gas space, the sensor element having at least one pump cell, including at least two electrodes and at least one solid electrolyte connecting the electrodes, at least one first electrode of the pump cell being able to be acted upon with gas from the measuring gas space, at least one second electrode of the pump cell being connected to at least one reference channel, a check being carried out in the method to ascertain whether a pump current is limited by the pump cell by acting upon the first electrode with gas or whether the pump current is limited by the reference channel. This document does not describe either the diagnosis of the rich measuring ability or the possibility of creating rich gas components in the measuring gas space in a targeted manner for diagnosing the rich measuring ability of the lambda sensor.

German Patent Application No. DE 102010039188 A1 describes a method for detecting at least one property of a gas in a measuring gas space, in particular for detecting a gas component of the gas, at least one sensor element being used with at least one cell, the cell including at least one first electrode, at least one second electrode and at least one solid electrolyte connecting the first electrode and the second electrode, the first electrode being able to be acted upon with the gas from the measuring gas space, the second electrode being connected to at least one reference gas space, the reference gas space being configured to store a supply of the gas component of the gas, the method including at least two operating modes:

at least one measuring mode, the cell being operated as a pump cell in the measuring mode and the property being deduced from at least one pump current through the pump cell, and at least one diagnostic mode, a storage capacity of the reference gas space being tested in the diagnostic mode, at least one measured variable influenced by a Nernst voltage applied to the cell being detected and the storage capacity being deduced from the measured variable.

This document describes how the oxygen storage capacity within the lambda sensor may be influenced with the pump current. In addition, measuring modes are described, including details of the exhaust gas measurement in the case of engines operated in lean mode, in particular diesel engines. However, they do not discuss the diagnosis of the rich measuring ability.

German Patent Application No. DE 102010039392 A1 describes a device for detecting an oxygen component of a gas in a measuring gas space which includes at least one sensor element, the sensor element having at least one Nernst cell including at least one first electrode, at least one second electrode and at least one solid electrolyte connecting the first electrode and the second electrode, the first electrode being able to be acted upon by gas from the measuring gas space, the second electrode being situated in a reference gas space, the device also including at least one control, the control being configured to detect a voltage of the Nernst cell, the control also including an admission device for generating a reference pump current through the Nernst cell, the admission device being configured in such a way that a difference $\Delta I_{prel}$ of the reference pump currents amounts to no more than 50% of reference pump current $I_{prel}$ averaged over the air ratio ranges in the rich air ratio range and in the lean air ratio range. This document also describes the wiring of the exhaust gas sensor but without any description of or solution to the problems of diagnosing the rich measuring ability of engines being operated in lean mode.

SUMMARY

An object of the present invention is therefore to provide a method and a device, which make it possible to carry out a test of the reliability of an exhaust gas sensor when determining the composition of a rich exhaust gas mixture without applying rich exhaust gas to the exhaust gas sensor.

The object of the present invention relating to the method may be achieved due to the fact that, in a first phase, such a high voltage is applied between the first electrode and the second electrode that the reference gas channel is filled with additional oxygen by decomposition of water and/or carbon dioxide, and in a second phase, a pump current is used in a circuit containing the first electrode and the second electrode to evaluate the measuring ability. In the first phase, in a so-called "breathing mode," the reference gas channel used as the oxygen storage is filled with oxygen. During this phase, the output signal of the exhaust gas sensor is not suitable for determining a lambda value of the gas mixture. In the second phase, the electrical current is determined in the measuring circuit including the first electrode, the second electrode, the ceramic base body and control electronics. The value of the pump current in the system is determined by the electrode array, the materials involved and the compositions of the gas mixtures present at the electrodes, and this value is determined as an example on the basis of the voltage drop at a measuring resistor, which has been looped into one of the supply lines of the electrodes. The height and direction of the current are used for evaluating the measuring ability of the exhaust gas sensor based on empirical values and plausibility considerations.

This method is suitable in particular when a rich measuring ability of the exhaust gas sensor is determined as a measuring capability. Operating conditions, such as those during operation with a rich exhaust gas, occur temporarily on returning to a measuring mode of the exhaust gas sensor due to the reference gas channel being filled with oxygen. During normal measuring operation of the exhaust gas sensor in a lean exhaust gas mixture, for example, in an internal combustion engine operated with diesel fuel, oxygen diffuses out of the exhaust gas through a diffusion barrier and into the electrode cavity of the exhaust gas sensor, where a lambda value of approximately lambda=1 prevails due to the operating strategy. The oxygen diffused into the electrode cavity is incorporated into the base body of the exhaust gas sensor at the first electrode, which is also referred to as an internal pump electrode (IPE), which is made of an ion-conducting ceramic and is transported into the reference gas channel via the second electrode, which is also referred to as the exhaust air electrode (EAE). During the so-called breathing mode, a higher pump voltage is applied to the first and second electrodes than during normal measuring operation. Additional electrochemical reactions take place at the first electrode in this way, so that additional oxygen ($O_2$) is separated from the carbon dioxide ($CO_2$) and water vapor ($H_2O$) present in the exhaust gas and is transported into the reference gas channel. During the reaction at the first electrode, rich gas components hydrogen ($H_2$) and carbon monoxide (CO) are thus formed and released into the electrode cavity. This therefore results in an actual rich gas mixture having a lambda value of lambda <1 in the electrode cavity, although the gas mixture in the exhaust gas channel is still lean and has lambda >1.

If the base body is made of zirconium dioxide ($ZrO_2$), then the following reactions take place at the first electrode (IPE) during breathing operation:

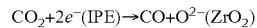

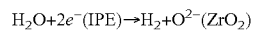

where $e^-$ denotes one electron and $O^{2-}$ denotes an oxygen ion having a double negative charge. The following reaction takes place at the second electrode (EAE):

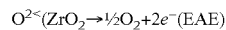

where $\frac{1}{2}O_2$ denotes the half of an oxygen molecule, the generation of which is the actual goal of the breathing mode. The occurrence of CO and $H_2$ is a side effect, which is utilized to determine the rich measuring ability according to the present invention. It is advantageous that the breathing mode is already provided as a program sequence in the control and need not be introduced additionally for implementation of the method according to the present invention.

In the second phase, the elevated pump voltage is reduced, and the exhaust gas sensor returns to the measuring mode. Here, the rich gas mixture in the electrode cavity is initially oxidized until reaching a lambda value of approximately lambda=1. The oxygen required for this purpose is withdrawn from the reference gas channel and supplied to the first electrode (IPE) of the pump cell. An additional amount of oxygen is withdrawn from the lean exhaust gas and passes through the diffusion barrier into the electrode cavity.

During the second phase, conditions thus prevail at the exhaust gas sensor as during a measuring operation using a rich exhaust gas mixture:

transport of oxygen from the reference gas channel into the electrode cavity oxidation of rich gas components at the first electrode using oxygen supplied there direction of electric current and mode of operation in the electrical measuring circuit correspond to rich exhaust gas mixture.

Due to the oxygen transport, a negative current pulse occurs briefly in the measuring circuit in the second phase. Upon returning to the measuring mode, this current pulse is utilized for diagnosing the measuring ability. If the current pulse does not occur, it is concluded that there is a defect in the measuring circuit or in the exhaust gas sensor.

The method according to the present invention advantageously makes use of the fact that the second phase is used with oxygen transport from the reference gas channel to the electrode cavity for evaluating the rich measuring ability of the exhaust gas sensor. A rich measuring operation may be tested under conditions such as those which also occur with an actual rich exhaust gas from the internal combustion engine. The direction of the electric current and the mode of operation in the entire electrical measuring circuit are similar in particular to those during the measuring operation using an exhaust gas mixture having a lambda value of lambda <1. Upon returning from the breathing mode to the measuring mode, a current pulse occurs due to the rich measuring operation using rich exhaust gas in the electrode cavity which is utilized for the diagnosis. If the negative pump current pulse does not occur, it is concluded that there is a defect in the measuring circuit or the exhaust gas sensor. Through a suitable choice of frequency of the "breathing mode" mode, it is possible to achieve the result that the requirements for maintaining the "in use monitor performance ratio" (IUMPR) are maintained.

An improvement in the accuracy of the method according to the present invention may be achieved in that operating parameters and/or function values are additionally used during the "breathing mode" for evaluating the measuring ability of the exhaust gas sensor and in that at least the voltage between the first electrode and the second electrode, a current flowing through a first and/or second supply line to the first and second electrodes, and/or a curve of the voltage and/or current over time is/are used as function values either individually or in a combination of measures. The voltage between the first electrode and the second electrode is the so-called pump voltage and the current through the supply lines is the so-called pump current.

When there is a change in the pump voltage, a capacitive charge-reversal current occurs, which superposes the current induced by the oxygen transport. The method according to the present invention is therefore advantageously improved by taking into account a capacitive charge-reversal current flowing through the first and/or second supply line during the evaluation of the measuring ability of the exhaust gas sensor when there is a change in voltage between the first electrode and the second electrode. Taking this capacitive charge-reversal current into account improves the accuracy of the diagnosis.

The object of the present invention relating to the device may be achieved by the fact that a circuit or program sequence for acting upon the exhaust gas sensor in a first phase with a voltage between the first electrode and the second electrode is provided in the control for transporting oxygen into the reference gas channel and for determining a pump current in a second phase in a circuit containing the first electrode and the second electrode for evaluating the measuring ability. This addition to the control makes use of the fact that rich gas components are formed by electrochemical reactions at the first electrode in an electrode cavity during the first phase, which together with the oxygen in the reagent gas channel at the start of the second phase, result in a current pulse which is characteristic of operation with rich exhaust gas. If this current pulse does not occur, the diagnosis of the measuring ability is terminated with a negative outcome. This advantageously makes use of the fact that the exhaust gas from the internal combustion engine need not be switched to a rich operating mode and therefore an increased consumption and undesirable emissions during the diagnosis may be prevented.

The device is suitable in particular for diagnosis when the exhaust gas sensor is designed as a lambda sensor or as a nitrogen oxide sensor. The device and the method may therefore be adapted to structural differences in the exhaust gas sensors as needed but without departing from the basic idea.

The method and the device are advantageously used in particular for diagnosing a rich measuring ability of a lambda sensor in the exhaust gas channel of an internal combustion engine. This makes use of the fact that the exhaust gas from the internal combustion engine need not be switched to rich operation and therefore an increased consumption and undesirable emissions during the diagnosis may be prevented.

BRIEF DESCRIPTION OF THE DRAWINGS

The present invention is described in greater detail below on the basis of one exemplary embodiment illustrated in the FIGURE.

FIG. 1 shows a single-cell exhaust gas sensor.

DETAILED DESCRIPTION OF EXAMPLE EMBODIMENTS

FIG. 1 shows a single-cell exhaust gas sensor 10 including a base body 13 and a gas inlet 12, which is open toward an exhaust gas channel of an internal combustion engine (not shown here). Exhaust gas sensor 10 functions as a lambda sensor for determining the composition of the air-fuel mixture supplied to the internal combustion engine. Base body 13 is manufactured from a solid electrolyte, for example, yttrium-stabilized zirconium dioxide, which is ion-conducting at the operating temperature, and with a suitable layout of electrodes and gas supply lines, is suitable for determining a concentration of certain components of a gas composition. Exhaust gas 11 passes through a diffusion barrier 14 into an electrode cavity 15 via gas inlet 12. Diffusion barrier 14 is a porous element, which at least largely prevents an extra flow of gas out of gas inlet 12 into electrode cavity 15 or in the opposite direction and enables only a diffusion transport. A portion of the wall of base body 13 is occupied by a first electrode 16 in electrode cavity 15, which is guided outward via a second supply line 21. Base body 13 also has a reference gas channel 18, which is filled with a porous gas-permeable medium and whose wall is partially occupied by a second electrode 17. Second electrode 17 is guided outward via a first supply line 20. First electrode 16 is also referred to as an internal pump electrode (IPE). Reference gas channel 18 is also referred to as an exhaust air channel (EAC), and second electrode 17 is also referred to as an exhaust air electrode (EAE). First electrode 16 and second electrode 17 are situated in the interior of base body 13, which is designed to have a layered structure in the exemplary embodiment shown here. First electrode 16, second electrode 17 and the solid electrolyte of base body 13 situated in between together form a pump cell.

In addition, exhaust gas sensor 10 in the exemplary embodiment shown here includes a heating element 24 including an insulation layer 25 which surrounds heating element 24 and prevents electrical contact with other components of exhaust gas sensor 10 at operating temperature. Heating element 24 is supplied with operating voltage via a first heating line 22 and a second heating line 23. The operating voltage is regulated by an assigned control in such a way that a predefined internal resistance of the pump cell is set. The voltages at first and second electrodes 16, 17 are also determined or predetermined in the control of the internal combustion engine, and the currents in first and second supply lines 20, 21 are determined or predetermined. The internal pump electrode or first electrode 16, which is acted upon by exhaust gas, is connected to virtual ground of the control as an example of an implementation. This virtual ground applies to first electrode 16 a constant electrode potential relative to an electrical ground. However, second electrode 17 or exhaust air electrode is at a variable potential. A pump current $I_P$ through the pump cell is determined via a pump voltage source with the aid of a current measuring device, for example, with the aid of a measuring shunt. In conventional circuits, this takes place in such a way that a pump voltage $U_P$ of the pump voltage source is regulated via a feed at a noninverting input of an operational amplifier in order to set a higher pump voltage of 900 mV during a measurement in air but a lower pump voltage $U_P$ of 200 mV in the case of rich gas. A Nernst voltage $U_N$ appears between first electrode 16 and second electrode 17 depending on the composition of the exhaust gas.

Alternatively, a diagnosis is also possible during discontinuous digital operation of the electrochemical cell using a pulsating pump current.

According to the present invention, in preparation for a diagnosis of the rich measuring ability of exhaust gas sensor 10, a high pump voltage $U_P$ is temporarily applied between first electrode 16 and second electrode 17. In this way, reference gas channel 18 becomes filled with oxygen in this phase, which is referred to as the "breathing mode." During the breathing mode, the output signal of exhaust gas sensor 10 is not suitable for determining the lambda value. If reference gas channel 18 is sufficiently filled with oxygen, then rich operation occurring briefly upon return to normal measuring operation may be utilized for the diagnosis. This diagnosis provides at least a qualitative statement for the rich measuring ability without having to supply an actual rich gas mixture to exhaust gas sensor 10.

What is claimed is:

1. A method for diagnosing a measuring ability of an exhaust gas sensor in an exhaust gas channel of an internal combustion engine, the sensor having a storage volume in a reference gas channel, at least one first electrode facing an electrode cavity connected to the exhaust gas channel and a second electrode facing the reference gas channel, comprising:
applying such a high voltage between the first electrode and the second electrode in a first phase that the reference gas channel is filled with additional oxygen due to a decomposition of at least one of water and carbon dioxide; and
in a second phase, evaluating the measuring ability using a pump current in a circuit containing the first electrode and the second electrode;
wherein a rich measuring ability of the exhaust gas sensor is determined as the measuring ability.

2. A method for diagnosing a measuring ability of an exhaust gas sensor in an exhaust gas channel of an internal combustion engine, the sensor having a storage volume in a reference gas channel, at least one first electrode facing an electrode cavity connected to the exhaust gas channel and a second electrode facing the reference gas channel, comprising:
applying such a high voltage between the first electrode and the second electrode in a first phase that the reference gas channel is filled with additional oxygen due to a decomposition of at least one of water and carbon dioxide; and
in a second phase, evaluating the measuring ability using a pump current in a circuit containing the first electrode and the second electrode;
wherein the second phase is used with an oxygen transport from the reference gas channel to the electrode cavity for evaluating a rich measuring ability of the exhaust gas sensor.

3. The method as recited in claim 1, wherein at least one of operating parameters and function values, are additionally used during the first phase for evaluating the measuring ability of the exhaust gas sensor, and at least one of: i) the voltage between the first electrode and the second electrode, ii) a current flowing through a first or second supply line to the first and the second electrodes, iii) a curve of the voltage or current over time, are used.

4. A method for diagnosing a measuring ability of an exhaust gas sensor in an exhaust gas channel of an internal combustion engine, the sensor having a storage volume in a reference gas channel, at least one first electrode facing an electrode cavity connected to the exhaust gas channel and a second electrode facing the reference gas channel, comprising:
applying such a high voltage between the first electrode and the second electrode in a first phase that the reference gas channel is filled with additional oxygen due to a decomposition of at least one of water and carbon dioxide; and
in a second phase, evaluating the measuring ability using a pump current in a circuit containing the first electrode and the second electrode;
wherein in the evaluation of the measuring ability of the exhaust gas sensor, a capacitive charge-reversal current flowing through at least one of the first supply line and the second supply lines, is taken into account when there is a change in the voltage between the first electrode and the second electrode.

5. A method for diagnosing a measuring ability of an exhaust gas sensor in an exhaust gas channel of an internal combustion engine, the sensor having a storage volume in a reference gas channel, at least one first electrode facing an electrode cavity connected to the exhaust gas channel and a second electrode facing the reference gas channel, comprising:
applying such a high voltage between the first electrode and the second electrode in a first phase that the reference gas channel is filled with additional oxygen due to a decomposition of at least one of water and carbon dioxide; and
in a second phase, evaluating the measuring ability using a pump current in a circuit containing the first electrode and the second electrode;
wherein the method is used for diagnosing a rich measuring ability of a lambda sensor in an exhaust gas channel of an internal combustion engine.

6. A method for diagnosing a measuring ability of an exhaust gas sensor in an exhaust gas channel of an internal combustion engine, the sensor having a storage volume in a reference gas channel, at least one first electrode facing an electrode cavity connected to the exhaust gas channel and a second electrode facing the reference gas channel, comprising:
applying a voltage between the first electrode and the second electrode in a first phase, wherein in the first phase, the applied voltage being such a high voltage that the reference gas channel is filled with additional oxygen due to a decomposition of at least one of water and carbon dioxide; and
in a second phase which follows the first phase, reducing the voltage applied between the first electrode and the second electrode from the high voltage, and evaluating the measuring ability of the exhaust gas sensor using a pump current in a circuit containing the first electrode and the second electrode, wherein during the second phase, oxygen transports from the reference gas channel to the electrode cavity;
wherein during the second phase, conditions prevail at the exhaust gas sensor as would have prevailed in the case of a rich exhaust gas mixture, but without applying an actual rich exhaust gas mixture to the exhaust gas sensor.

\* \* \* \* \*